United States Patent [19]

Ferruti et al.

[11] 4,228,152

[45] Oct. 14, 1980

[54] POLYMERS CONTAINING PROSTAGLANDIN RADICALS, PROCESS FOR THEIR PREPARATION AND USE THEREOF

[76] Inventors: Paolo Ferruti, V.le Cassiodora, 24; Rodolfo Paoletti, V.le Regina Margherita, 43, both of Milan, Italy

[21] Appl. No.: 960,665

[22] Filed: Nov. 14, 1978

Related U.S. Application Data

[63] Continuation-in-part of Ser. No. 620,401, Oct. 7, 1975, abandoned.

[30] Foreign Application Priority Data

Oct. 7, 1975 [IT] Italy .................. 28419 A/75

[51] Int. Cl.$^2$ .................................. A61K 31/78
[52] U.S. Cl. .................................. 424/81; 424/19; 424/78; 525/329; 525/379; 525/380; 525/382; 525/384
[58] Field of Search .................. 128/260; 424/19–22, 424/81, 78; 526/16, 52.2, 52.3, 52.5, 54

[56] References Cited

U.S. PATENT DOCUMENTS

| | | | |
|---|---|---|---|
| Re. 28,316 | 1/1975 | Banker et al. | 424/81 |
| 3,764,477 | 10/1973 | Lehmann et al. | 424/81 |
| 3,811,444 | 5/1974 | Heller et al. | 128/260 |
| 3,898,986 | 8/1975 | Zaffaroni | 128/130 |
| 3,932,656 | 1/1976 | Ramwell et al. | 424/16 |
| 4,062,855 | 12/1977 | Graham et al. | 260/295 PA |
| 4,145,320 | 3/1979 | Ferruti et al. | 424/81 X |

FOREIGN PATENT DOCUMENTS

| | | | |
|---|---|---|---|
| 2363963 | 7/1972 | Fed. Rep. of Germany | 128/260 |
| 869149 | 5/1961 | United Kingdom | 424/81 |

OTHER PUBLICATIONS

Ferruti et al., Polymer, vol. 13, pp. 462–464 (Oct. 1972).
Ferruti, Researches on Polymers, Dorprecht (Holland, Dec. 1973), pp. 73–101.
Ferruti et al., J. of Polymer Science, Polymer Chem. Ed., vol. 12, pp. 553–559 (1974).

*Primary Examiner*—Carman J. Seccuro
*Attorney, Agent, or Firm*—Stevens, Davis, Miller & Mosher

[57] ABSTRACT

There are disclosed non-toxic polymers having a molecular weight between 1,000 and 1,500,000 and containing prostaglandin radicals directly connected or connected through an oxyalkylenic, aminoalkylenic, or oxyaminoalkylenic chain to a polyacrylic or polymethacrylic backbone. Upon entry of the polymer into the body, the prostaglandin radicals are hydrolyzed causing free prostaglandins to be released in the body. Methods for making the non-toxic polymers and therapeutic compositions containing the non-toxic polymers are also disclosed.

13 Claims, No Drawings

POLYMERS CONTAINING PROSTAGLANDIN RADICALS, PROCESS FOR THEIR PREPARATION AND USE THEREOF

This application is a continuation-in-part of copending application Ser. No. 620,401 filed Oct. 7, 1975, now abandoned.

The present invention refers to new polymers characterized by the presence of prostaglandin radicals bound to a polymeric matrix in such a way to be hydrolyzed and thus to release free prostaglandins in biological systems.

More precisely, the present invention refers to a high polymers containing prostaglandin radicals bound to a macromolecular matrix by ester or amidic bonds, which are gradually hydrolyzed in a predetermined way in biological systems.

It is well known that prostaglandins represent one of the most interesting developments in the biomedical field during last years.

From the chemical point of view prostaglandins are polyunsaturated hydroxy acids with a skeleton of 20 carbon atoms, partially cyclized to form a ring of 5 carbon atoms. Prostaglandins have been classified in several series of which two have significant biomedical effect. These two major series differ only because one (PGF) contains two hydroxyl groups in the 5 carbon atom ring, and the other (PGE), a keto group and a hydroxyl group in the same ring.

lation of arterial pressure, platelets aggregation, gastric secretion.

From the practical point of view, a considerable body of published evidence demonstrates that prostaglandins are of use to solve the problem of birth control, as preventing agents if administered at appropriate time and doses, or by inducing abortion.

However, the great hopes in this fields have been partially non-substantiated by a practical use of prostaglandins, due to the insurgence of collateral effects which cannot be eliminated or controlled. For example, in order to obtain the desired effect of fertility control or abortion induction, prostaglandins should be given at such large doses and for such prolonged periods, that other biological effects of prostaglandins become evident, as the induction of hypotensive or hypertermic crisis, intestinal smooth muscle contractions and thus vomit and diarrhea, headache, decrease of the pain threshold in muscles and articulations and platelets aggregation.

We have unexpectedly found that new polymers containing prostaglandin radicals bound to the macromolecular matrix through covalent bonds of esteric or amidic type can be synthetized. Such polymers in biological systems are gradually hydrolysed releasing predetermined amounts of prostaglandins over predetermined time intervals.

Such polymer classes are non-toxic for mammalian arganisms, give rise to non toxic metabolites and can be predesigned from the point of view of the chemical

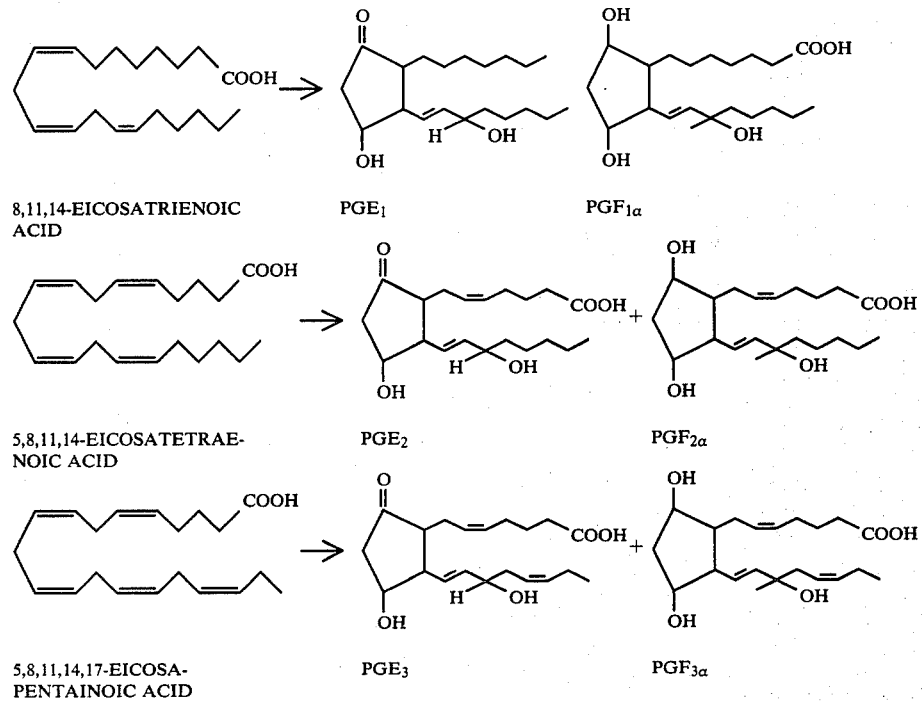

Subclasses are also known characterized by the presence of a double bond in a fixed position or by the presence of more than one double bond. In all cases prostaglandins present a carboxyl and at least one hydroxyl group free to react.

According to recent studies, prostaglandins are responsible in the organism of a great variety of physiological and pharmacological effects, from fertility control to stimulation of smooth muscle contraction, regunature, of the molecular weight of the percentage of prostaglandin radicals contained in the macromolecular complex and of the type of chemical bonds connecting the prostaglandin radicals with the macromolecular matrix. This may be done in such a way to insure the presence in blooc and tissues of strictly controlled concentrations of prostaglandins for the desired time intervals.

The presence of excess prostaglandins in the organism is therefore avoided and undesirable side effects due to prostaglandins and/or their metabolites can be prevented or strongly reduced. Moreover and quite unexpectedly we have found that the new polymers with respect to free prostaglandins:

(a) have an "intensity" of effect at least three times stronger
(b) have an overall "activity" from 5 to 50 times higher
(c) present side-effects strongly reduced and practically negligible
(d) the side-effects do not increase at increasing doses
(e) may be specifically construed so as to provide the same prostaglandin as a drug hydrosoluble or liposoluble or as a gel, suitable to be used in the most different pathological situations
(f) besides to be strongly more useful in the same therapeutic fields, have some new peculiar field of application namely: intermediate metabolism of lipides and glycides, emathology.

Our new polymers are characterized by a polyvinylic backbone to which prostaglandins radicals are bound by covalent esteric or amidic bonds, either directly or through side chains. Preferably the fundamental polyvinylic structure is a polymer of acrylamide or methacrylamide, (A) acrylic acid or methacrylic acid (B):

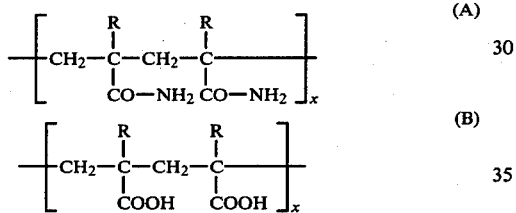

where R is H or CH$_3$.

If polymers comprised in the formula A or B are directly reacted with prostaglandins, the new polymers of formula (A') or (B') are prepared:

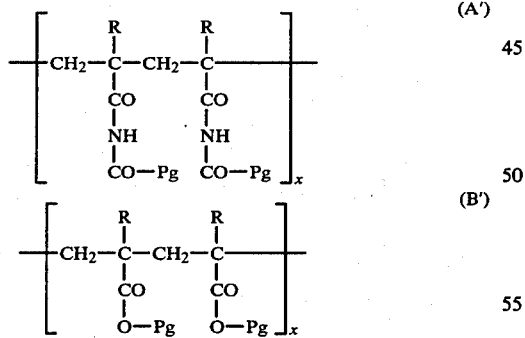

where Pg represents the prostaglandin radical bound to the macromolecular backbone in the first instance through the terminal carboxyl-group and in case of polymers (B') through a hydroxy-group, most probably through the hydroxy-group on the aliphatic side-chain.

Alternatively the prostaglandin's radicals —COPg or —OPg may be bound to the macromolecular backbone, particularly of the type (B), through side-chains which are the radicals of alkylene-diamines (NH$_2$—(CH$_2$-)$_n$—NH$_2$), hydroxy-alkyl-amines (HO—(CH$_2$)$_n$—NH$_2$), alkylene-dihdroxy compounds (HO—(CH$_2$)$_n$—OH)

where (CH$_2$)$_n$ represents a linear or branched alkyl radical containing from 2 to 12 carbon atoms:

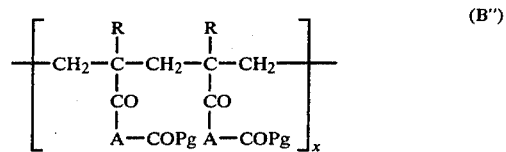

where A represents one of the radicals —O—(CH$_2$-)$_n$—NH—, —O—(CH$_2$)$_n$—O—, —NH—(CH$_2$-)$_n$—NH— as above defined.

These new polymers, according to the invention, are preferably prepared through the following processes:

(a) preparation of acrylic monomers containing reactive groups chosen in the group comprising 1-acryloilbenzotriazole, 1-acryloil methoxybenzotriazole, 1-acryloilmethylbenzotriazole, 1-acryloil imidazole, N-acryloilsuccinimide and N-2,4,5-trichlorophenylacrylamide; homopolymerization of these monomers or their copolymerization with different vinylic monomers; reaction of the above polymers or copolymers with prostaglandins through the reactive groups of the polymeric matrix;

homopolymerization of acrylic acid or its copolymerization with other vinylic monomers; reaction of these polymers or copolymers with carbonyldiimidazole in order to introduce reactive groups of acetylimidazolide type; reaction of this macromolecular substance with prostaglandins;

(c) preparation of homopolymers or copolymers containing reactive groups as indicated under (a); reaction of these macromolecular substances with alkylene-diamines, hydroxyalkylamines or alkylenedihydroxy compounds in order to obtain side chains containing reactive hydroxyl or aminic groups; reactions of these new macromolecular substances with prostaglandins.

Acrylic polymers and copolymers containing reactive functional groups as described, and also acrylic polymers and copolymers containing side chains comprising hydroxy or amino groups, are prepared according to methods pertaining to the art and described in particular in the following publications:

(1) Encyclopedia of Polymer Science and Technology, Vol. 1, pages 177–273
(2) Polymer—1972, Vol. 13, Oct. 462–464
(3) Reactions on Polymers—Holland—December 1973
(4) J. of Polymer Science—Vol. 12–553–559(1974).

The reactive macromolecular structure thus prepared is reacted with prostaglandins in a suitable inert, anhydrous, organic solvent, under inert gas atmosphere.

The reaction temperature may vary within 10° and 80° C. and the reaction time is comprised within a minimum time of 5 hours up to 75 hours.

The temperature and the time of the reaction depend of course from the basic macromolecular structure to be reacted. The macromolecular matrix is prepared with a determined percentage of reactive groups according to the desired percentage of prostaglandins in the final product. The new polymers with a fundamental polymethacrylic structure are more slowly hydrolyzed than the corresponding acrylic polymers and therefore they release more slowly the prostaglandins thus prolonging the biological activity and reducing the side effects. The polymers, according to the invention may be water soluble or insoluble (oil insoluble) and can be prepared in form of hydrophylic, but water insoluble gels.

If water soluble polymers are desired, hydrophylic monomers must be used, particularly monomers selected in a group comprising 1-acryloil-4-methyl piperazine, N-acryloil morpholine, N-vinylpyrolidone, which monomers copolymerise smoothly and with almost quantitative yields with the activated acrylic monomers.

The same monomers are used if hydrophylic gels are desired, but in this case difunctional comonomers are added in the range of 0.5 to 30% in order to obtain a crosslinked product. These difunctional monomers are preferably chosen from the group consisting of divinylbenzene or bis-acrylamides such as methylene bisacrylamide, N,N'bisacryloil piperazine or N,N'bis acryloil N,N'-dimethylethylene diamine.

The new polymers, according to the invention, can be administered with any procedure already in use for the free prostaglandins and particularly by intravenous, intraamniotic, intrauterine or intravaginal routes.

They may be administered as a therapeutic composition in the form of an aqueous solution, a water-or oil-suspension, and a water-insoluble gel. The aqueous solutions are preferably used for parenteral or intravenous injection; the water- or vegetable oil-suspensions are preferably used for oral administration, the gels are preferably used for intrauterine or intravaginal administration.

The amount of the prostaglandine—containing polymer to be administered is easily determined once, it has been determined how many times more active than the corresponding free prostaglandin, the polymer is.

This activity is determined with tests like the following ones, although other tests could be used.

The experiments have been carried out by using anesthetized cats weighting 2.100 kg. Anaesthesia has been induced with ethyl ether and maintained with a solution of chloralase and urethane (80:100) given intravenously through the femoral vein. Then trachea and one femoral artery are cannulated for pressure registration.

A baloon is introduced in the stomach for the direct registration of smooth muscle motility.

The results are summarized in the following Table 1. The polymer employed and shortly indicated with (A) is that prepared as described in Example n. 1.

TABLE 1

| Treatment i.v. | Dose mg/kg | Mean arterial pressure (decrease in % in mmHg) | Activation of stomach motility (durat. in minutes) | Bronchospasm + (durat. in sec.) |
|---|---|---|---|---|
| $PGF_{2\alpha}$ | 1 | 63 | 42 | 36.17 |
| Polymer A corresponding to free $PGF_{2\alpha}$ | 0.375 | 63 | 112 | 18.45 |
| Polymer A corresponding to free $PGF_{2\alpha}$ | 0.750 | 53 | 172 | 18.52 |
| Polymer obtained before the reaction with $PGF_{2\alpha}$ | 12.135 | 0 | 0 | 0 |

+ reduction of air flux

In the Table the decrease in arterial pressure is an index of "intensity" of action, while the duration of activation of stomach motility is an index of "duration" of action. Both these are primary, positive effects of prostaglandins. The duration of bronchospasm is on the contrary an index of the undesired side-effects.

The data of Table 1 demonstrate that controlling through the administration of prostaglandine-containing polymers, the amount and the administration time of prostaglandins to the organism, it has become possible:
 (a) to produce an effect three times more intense than with the same free prostaglandin (the same effect is produced with 0.375 mg of bound $PGF_{2\alpha}$ rather than with 1 mg of free $PGF_{2\alpha}$ - Mean arterial pressure test)
 (b) to produce an effect three times more prolonged with doses of equivalent activity (Activation of stomach motility test)
 (c) to strongly reduce side-effects. Side effects do not increase at increasing doses.

From (a) and (b) it is deduced that the polymer (A) is nearly nine times more active than the free prostaglandin, since we can achieve a nearly 3 times more prolonged effect with ⅓ of dose.

Generally speaking it can be said that the polymers of the invention are from 5 to 50 times more active than the corresponding free prostaglandine, consisting always as "activity" the duration in the time of an effect of given intensity.

Moreover it has to be noted that while a prostaglandin may be put at disposal of the physician as a drug hydrosoluble or liposoluble or as a gel, with the new polymers according to the invention the same prostaglandin may be produced in the organism while administering it in any desired and suitable form only modifying the macromolecular structure to which the prostaglandin is bound.

It is thus possible to use the same prostaglandin in the most different pathologic situations, both acute and cronic, and in whatever part of the organism they arise.

To the end of better clarifying the objects of the present invention, we furnish hereinafter some preparative examples of the new polymers according to the invention, which examples have to be intended as merely illustrative but in no way limitative of the invention.

EXAMPLE 1

(a) A mixture consisting of 1 g of 1-acryloilbenzotriazole, 9 g of 1-acryloil-4-methyl-piperazine, 100 mg of azodiisobutyronitrile and 50 ml of anhydrous dioxane is heated at 60° C. over 40 hours, under argon atmosphere.

The reacted mixture is poured into one liter of anhydrous ethylic ether and a polymer separates, with nearly 100% yield, which contains 10% by weight of acryloilbenzotriazole.

(b) 300 mg of the polymer obtained under (a) are dissolved in 1.5 ml of a 2.5% solution of triethylamine in pure and anhydrous chloroform and then placed in a vial having a 20 ml capacity. 7.5 ml of a solution containing 1% by weight of a prostaglandine $PGF_{2\alpha}$ and one mole of triethylamine for each mole of $PGF_{2\alpha}$ dissolved in chloroform are added; the whole is stirred, air is replaced by argon and the vial, melded always keeping under argon atmosphere, is placed in a thermostatized bath kept at 60°±0.1° C., in the dark, over 72 hours.

After this time the content of the vial is poured in 400 ml of ether, the precipitate is washed with ether and dried at room temperature and 0.001 mm Hg.

The so prepared polymer is able to set free the whole of the contained prostaglandin which is nearly the 18% of the polymer weight.

Copolymers containing higher or lower amounts of prostaglandins have been prepared starting from acrylic copolymers comprising higher or lower amounts of 1-acryloilbenzotriazole.

Polymers showing equally good characteristics of solubility in water have been prepared starting from N-vinylpyrolidone and N-acryloilmorpholine rather than from 1-acryloil-4-methylpiperazine.

EXAMPLE 2

(a) A copolymer of 1-acryloil-4-methylpiperazine and acrylic acid, containing 4.54% of this latter monomer, is prepared under tha same conditions of example 1(a).

(b) 1 g of the polymer prepared under (a) is dissolved in 25 ml of anhydrous chloroform or of pyridine, is treated with 0.13 g of N,N-carbonyldiimidazole and left to rest for 3 hours.

After this time the polymer is precipitated with anhydrous ethyl ether and dried at 0.001 mmHg while constantly excluding the presence of moisture.

(c) 250 mg of the copolymer thus obtained are dissolved into 10 ml of pure anhydrous chloroform and are reacted with a chloroformic solution of prostaglandin $PGF_{2\alpha}$ in the identical manner described in the example 1(b). In this case a heating of 24 hours only is sufficient.

A polymer containing nearly 18% of hydrolizable $PGF_{2\alpha}$ is obtained with a yield of about 100%.

EXAMPLE 3

In the identical manner described under Example 2 a copolymer is prepared while using methacrylic rather than acrylic acid. A copolymer is obtained containing 5.42% b.w. of methacrylic units and about 18% b.w. of prostaglandin $PGF_{2\alpha}$. The prostaglandin is released from this polymer by hydrolysis in a biological system, in a longer time than from the polymer of the preceding example.

According to the procedure described in detail in Example 1, the following new polymers have been also prepared:

| | | |
|---|---|---|
| 1-acryloyl-methoxy-benzotriazole | 10% | |
| 1-acryloyl-4-methylpiperazine | 90% | I |
| ethanolamine | | |
| $PGF_{2\alpha}$ | | |
| 1-acryloyl-methyl-benzotriazole | 20% | |
| N-acryloyl-morpholine | 80% | II |
| ethylenediamine | | |
| $PGF_{2\alpha}$ | | |
| 1-acryloyl-methyl-benzotriazole | 20% | |
| 1-acryloyl-morpholine | 80% | III |
| ethylenediamine | | |
| $PGF_{2\alpha}$ | | |
| 1-acryloyl-methyl-benzotriazole | 50% | |
| N-acryloyl-morpholine | 50% | IV |
| ethylenediamine | | |
| $PGF_{2\alpha}$ | | |
| N-acryloxysuccinimide | 25% | |
| N-vinylpyrrolidone | 75% | V |
| ethyleneglycol | | |
| $PGF_{2\alpha}$ | | |
| N-acryloxysuccinimide | 40% | |
| N-vinylpyrrolidone | 60% | VI |
| ethanolamina | | |
| $PGF_{2\alpha}$ | | |
| N-2,4,5-trichlorophenylacrylamide | 10% | |
| 1-acryloyl-4-methylpiperazine | 90% | VII |
| ethylenediamine | | |
| $PGF_{2\alpha}$ | | |
| N-2,4,5-trichlorophenylacrylamide | 20% | |
| 1-acryloyl-4-methyl-piperazine | 80% | VIII |
| ethanolamine | | |
| $PGF_{2\alpha}$ | | |

In the above polymers, for each unit of the first indicated monomer (activated monomer), one unit of the third component and of prostaglandin are present.

Each polymer having the above described composition has been used in the same pharamcological tests previously described for the polymer of Example 1.

An amount of each polymer was administered corresponding to a content of (and thus able to release) 0.375 and 0.750 mg/kg of the $PGF_{2\alpha}$ prostaglandin: the obtained results are thus comparable among them and with the dose of 1 mg/kg of prostaglandin $PGF_{2\alpha}$.

Said results are collected in the following Tables and clearly demonstrate that all the claimed polymers have nearly the same activity.

TABLE 2

| | | Mean arterial pressure - decrease in % in mm Hg | | | | | | | |
|---|---|---|---|---|---|---|---|---|---|
| | A | I | II | III | IV | V | VI | VII | VIII |
| Free Prostaglandin 1 mg/kg | 63 | | | | | | | | |
| Polymer 0.375 mg/kg* | | 63 | 61.7 | 63.1 | 61 | 62.5 | 60.9 | 61.8 | 62.3 | 61.4 |
| Polymer 0.750 mg/kg* | | 53 | 51.4 | 53.3 | 52.7 | 52 | 54.1 | 53 | 52.9 | 53.7 |
| Macromolecular backbone (variable amounts for each polymer) | | 0 | 0 | 0 | 0 | 0 | 0 | 0 | 0 | 0 |

*Amount of prostaglandin bound to the polymer administered;

TABLE 3

| | | Activation of stomach motility - duration in minutes | | | | | | | |
|---|---|---|---|---|---|---|---|---|---|
| | A | I | II | III | IV | V | VI | VII | VIII |
| Free Prostaglandin 1 mg/kg | 42 | | | | | | | | |
| Polymer 0.375 mg/kg* | | 112 | 108.6 | 114.2 | 112.2 | 110.4 | 112.3 | 113 | 107.9 | 112.5 |
| Polymer 0.750 mg/kg* | | 172 | 165.2 | 173.7 | 180 | 168.8 | 171.5 | 172.5 | 164.9 | 177.2 |

TABLE 3-continued

| | Activation of stomach motility - duration in minutes | | | | | | | | |
|---|---|---|---|---|---|---|---|---|---|
| | A | I | II | III | IV | V | VI | VII | VIII |
| Macromolecular backbone (variable amounts for each polymer) | 0 | 0 | 0 | 0 | 0 | 0 | 0 | 0 | 0 |

*Amount of prostaglandin bound to the polymer administered.

TABLE 4

| | Bronchospasm - duration in seconds | | | | | | | | |
|---|---|---|---|---|---|---|---|---|---|
| | A | I | II | III | IV | V | VI | VII | VIII |
| Free Prostaglandin 1 mg/kg | 36.17 | | | | | | | | |
| Polymer 0.375 mg/kg* | | 18.4 | 18.2 | 17.7 | 19 | 18.5 | 18 | 17.5 | 19.3 | 17.9 |
| Polymer 0.750 mg/kg* | | 18.5 | 17.8 | 18.3 | 19.3 | 18.5 | 18.2 | 17.5 | 19 | 18.8 |
| Macromolecular backbone (variable amounts for each polymer) | 0 | 0 | 0 | 0 | 0 | 0 | 0 | 0 | 0 |

*Amount of prostaglandin bound to the polymer administered.

What is claimed is:

1. A non-toxic polymer having a molecular weight between 1,000 and 1,500,000 containing prostaglandin radicals bound to a polyacrylic or polymethacrylic backbone either directly or through oxyalkylenic, aminoalkylenic or oxyaminoalkylenic chains, said polymer containing units of the formula

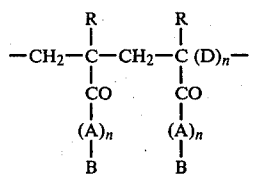

wherein R represents H or $CH_3$, A represents an alkylene radical terminated at both ends with an —NH— or —O— group, n represents 0 or 1 in both occurences, B represents —OPg or —CO—Pg wherein Pg represents a prostaglandin residue, and D represents a divalent radical supplied by a comonomer selected from the group consisting of 1-acryloyl-4-methyl piperazine, N-acryloyl morpholine, N-vinyl pyrrolidone, divinylbenzene, methylene bisacrylamide, N,N'-bisacryloyl piperazine, N,N'-bisacryloyl N,N'-dimethylethylene diamine.

2. The non-toxic polymer of claim 1 wherein the radical A is derived from compounds selected from the group consisting of N,N-dihydroxy ethyl-1,3-propanediamine, ethanolamine, ethylene diamine and ethyleneglycol.

3. The process of claim 1 wherein said monomer is homopolymerized.

4. The process of claim 1 wherein said monomer is copolymerized with monomers selected from the group consisting of 1-acryloyl-4-methyl piperazine, N-acryloyl-morpholine, N-vinylpyrrolidone, divinylbenzene, methylenebisacrylamide, N,N'-bisacryloylpiperazine, N,N'-bisacryloyl-N,N'-dimethylethylenediamine.

5. A process for the preparation of the non-toxic polymer of claim 1 comprising
polymerizing acrylic acid or methacrylic acid,
reacting the resulting polymer with carbonyldiimidazole to introduce reactive imidazolic groups into the chain of the resulting polymer, and
reacting the treated polymer with prostaglandins.

6. The process of claim 5 wherein acrylic acid or methacrylic acid is homopolymerized.

7. The process of claim 5 wherein acrylic acid or methacrylic acid are copolymerized with monomers selected from the group consisting of 1-acryloyl-4-methylpiperazine, N-acryloyl morpholine, N-vinylpyrrolidone, divinylbenzene, methylenebisacrylamido, N,N'-bisacryloylpiperazine, N,N'-bisacryloyl-N,N'-dimethylethylenediamine.

8. A process for the preparation of the non-toxic polymer of claim 1 containing prostaglandin radicals bound through oxyalkenic, aminoalkylenic or oxyaminoalkylenic chains to a macromolecular polyacrylic or polymethacrylic backbone comprising
polymerizing a monomer selected from the group consisting of 1-acryloyl benzotriazole, 1-acryloyl methoxy benzotriazole, 1-acryloyl methylbenzotriazole, 1-acryloyl imidazole, N-acryloyl succinimide, and N-2,4,5-trichlorophenylacrylamide to form a macromolecular polymer backbone,
reacting said backbone with a compound selected from the group consisting of an alkylenediamine, an hydroxyalkylamine, and a glycol, and
reacting the resulting polymer with prostaglandin.

9. The process of claim 8 wherein said monomer is homopolymerized.

10. The process of claim 8 wherein said monomer is copolymerized with monomers selected from the group consisting of 1-acryloyl-4-methylpiperazine, N-acryloylmorpholine, N-vinylpyrrolidone, divinylbenzene, methylenebisacrylamide, N,N'-bisacryloylpiperazine, N,N'-bisacryloyl-N,N'-dimethylethylenediamine.

11. The process of claim 8 wherein said compound is selected from the group consisting of N,N-dihydroxy ethyl-1,3-propanediamine, ethanolamine, ethylenediamine and ethyleneglycol.

12. A therapeutic composition containing a therapeutically effective dose of the polymer of claim 1 and a pharamceutically acceptable carrier.

13. A process for the preparation of the non-toxic polymer of claim 1 comprising:
polymerizing a monomer selected from the group consisting of 1-acryloyl benzotriazole, 1-acryloly methoxy benzotriazole, 1-acryloly methylbenzotriazole, and 1-acryloly imidazole, and
reacting the resulting polymer with prostaglandins, with the proviso that when the resulting polymer is a polyacrylolybenzotriazole, the reaction with prostaglandins is carried out in the presence of triethylamine.

* * * * *